(12) United States Patent
Yamada et al.

(10) Patent No.: US 10,603,160 B2
(45) Date of Patent: Mar. 31, 2020

(54) MEDICAL DEVICE AND METHOD FOR FORMING A PROTUBERANT REGION

(71) Applicant: Terumo Kabushiki Kaisha, Tokyo (JP)

(72) Inventors: Yukiko Yamada, Fujinomiya (JP); Eiko Igarashi, Fujinomiya (JP); Aya Saito, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 115 days.

(21) Appl. No.: 15/424,017

(22) Filed: Feb. 3, 2017

(65) Prior Publication Data

US 2017/0224472 A1    Aug. 10, 2017

(30) Foreign Application Priority Data

Feb. 8, 2016  (JP) ................................. 2016-022264

(51) Int. Cl.
| | |
|---|---|
| *A61F 2/12* | (2006.01) |
| *A61F 2/02* | (2006.01) |
| *A61F 2/00* | (2006.01) |
| *A61B 90/00* | (2016.01) |
| *A61M 25/10* | (2013.01) |

(52) U.S. Cl.
CPC ............. *A61F 2/12* (2013.01); *A61B 90/02* (2016.02); *A61F 2/0059* (2013.01); *A61F 2/02* (2013.01); *A61F 2210/0004* (2013.01); *A61F 2250/0003* (2013.01); *A61F 2250/0004* (2013.01); *A61M 2025/1054* (2013.01)

(58) Field of Classification Search
CPC ...... A61F 2/12; A61F 2250/003; A61B 90/02; A61M 2025/1054
See application file for complete search history.

(56) References Cited

U.S. PATENT DOCUMENTS

| | | | | |
|---|---|---|---|---|
| 2006/0058735 | A1* | 3/2006 | Lesh ..................... | A61F 2/0059 604/93.01 |
| 2010/0222802 | A1* | 9/2010 | Gillespie, Jr. .......... | A61B 90/02 606/192 |
| 2011/0213400 | A1* | 9/2011 | Ahmann ............ | A61B 17/7097 606/191 |
| 2015/0032208 | A1 | 1/2015 | Preissman | |

FOREIGN PATENT DOCUMENTS

| | | |
|---|---|---|
| JP | 2013-215584 | 10/2013 |
| WO | WO 2009/076147 | 6/2009 |

* cited by examiner

*Primary Examiner* — Suba Ganesan
(74) *Attorney, Agent, or Firm* — Jason H. Vick; Sheridan Ross, PC (57) ABSTRACT

Procedural methods are provided that are capable of forming a protuberant region, in which the surface of a living body protrudes, in a less-invasive manner and a medical device capable of forming the protuberant region in a less-invasive manner. A procedural method for forming a protuberant region, in which a surface of a living body protrudes, includes an introduction step of introducing a container having flexibility into the living body, a protuberant region forming step of forming the protuberant region, in which the surface of the living body protrudes, by filling the container with a filling material to expand the container, and a placement step of placing the expanded container in the living body.

5 Claims, 8 Drawing Sheets

MEDICAL DEVICE AND METHOD FOR FORMING A PROTUBERANT REGION

CROSS REFERENCE TO RELATED APPLICATIONS

The present application claims the benefit of priority, under 35 U.S.C. § 119(e), to Japanese Application No. 2016-022264, filed Feb. 8, 2016, entitled "Procedure Method and Medical Device," the entire disclosure of which is incorporated herein by reference in its entirety, for all that it teaches and for all purposes.

TECHNICAL FIELD

The present invention relates to a procedure and method for forming a protuberant region, in which the surface of a living body protrudes, and a medical device for use in the formation of the protuberant region.

BACKGROUND

Heretofore, there has been known a medical technology for protruding (distending) a part of the surface of a living body, such as breast augmentation and buttock augmentation.

For example, implants for use in breast augmentation are discussed in Japanese Patent Application No. JP-A-2013-215584 and in U.S. Patent Application Publication No. 2015/0032208, the entire contents of which are hereby incorporated herein by reference for all that they teach and for all purposes. These implants are configured to be deformed to a reduced-size shape when being introduced into a living body and to be expandable (restorable) in such a way as to form an intended protuberant region after being introduced into the living body. Furthermore, the above-mentioned implants are made from a pouched member previously filled with a gel-like material or a relatively soft member, such as silicone, in such a way as to be deformable from the above-mentioned reduced-size shape to the expanded shape.

Usually, in breast augmentation implant procedures, when the implant is introduced into the living body, a procedure that forms a perforation is made, which serves as an introduction area for the implant, and a delivery route, which is used to deliver the implant from the perforation to a placement site, is made. The size of the perforation and the size of the delivery route are determined based on the size of the implant taken when the implant is introduced. Therefore, since larger sized implants, taken when the implant is introduced into the living body, require larger perforations and delivery routes, an increased burden is imposed on a patient as the size of the implant increases.

SUMMARY

Technical Problem

In a procedure using the implants discussed in the patent references provided above, since the implant can be introduced into the living body while being reduced in size to some extent, a burden imposed on a patient can be somewhat relieved. However, since these implants are configured to have a bulk (volume) required for protruding the surface of the living body even when being introduced, there is a limit to the reduction in size of the implant taken when the implant is introduced and, thus, there is room for improvement in the invasiveness patients are subjected to.

Therefore, it is an object of the present disclosure to provide a procedural method capable of forming a protuberant region, in which the surface of a living body protrudes, in a less-invasive manner and a medical device capable of forming the protuberant region in a less-invasive manner.

Solution to the Problem

In some embodiments, the procedural method may include an introduction step of introducing a container having flexibility into a living body, a protuberant region forming step of forming a protuberant region, in which a surface of the living body protrudes, by filling the container with a filling material to expand the container, and a placement step of placing the expanded container in the living body.

In one embodiment, a medical device is described that includes a first catheter configured to be inserted into a living body and a second catheter having a distal portion to which a container having flexibility is detachably attached, wherein the first catheter includes a first lumen through which to deliver the container of the second catheter to a predetermined placement site in the living body, the second catheter includes a second lumen through which to deliver a filling material to inside the container, and the container forms a protuberant region, in which a surface of the living body protrudes, by being detached from the second catheter and placed at the placement site in a state of being filled with the filling material.

Advantages of the Present Disclosure

In some embodiments of the procedural method described herein, the flexible container in a contractive state may be introduced into the living body, and, after being introduced, the container can be filled with the filling material, so that the container is expansively deformed. Then, the container being expansively deformed in the living body forms a protuberant region, in which a surface of the living body protrudes (distends). According to this procedural method, when the container is introduced into the living body, since the inside of the container is in an empty state, the bulk of the container can be made small. This enables reducing the size of a perforation which is formed on the living body when the container is introduced into the living body and the size of a delivery route through which to deliver the container to the placement site, so that a less-invasive procedure can be implemented. Furthermore, according to the procedural methods described herein, since the filling material is retained in the container, the filling material can be prevented from undesirably dispersing or disappearing in the living body. Accordingly, the state of the expansively deformed container can be stably maintained, and the state of the formed protuberant region can be maintained in good condition over an intended period of time.

In some embodiments, a procedure using the first catheter, the second catheter, and the container having flexibility enables forming a protuberant region, in which a surface of the living body protrudes (distends). A perforation and a delivery route can be formed on and in the living body in respective sizes corresponding to the dimension (the dimension of a cross-section perpendicular to the axis) of the first catheter. Moreover, the dimension of the first catheter can be set to a small size according to the size, or bulk, of the container in an empty state. Accordingly, a burden imposed on the living body in forming the protuberant region can be reduced, so that a less-invasive procedure can be implemented. In some embodiments, since the filling material may be retained in the container, the filling material can be prevented from undesirably dispersing or disappearing in the living body. Accordingly, the state of the expansively deformed container can be stably maintained, and the state of the formed protuberant region can be maintained in good condition over an intended period of time.

DETAILED DESCRIPTION

Hereinafter, embodiments of the present disclosure will be described with reference to the accompanying drawings. Moreover, dimensional ratios illustrated in the drawings may be exaggerated for the purpose of illustration and may be different from the actual ratios.

Figure 1:
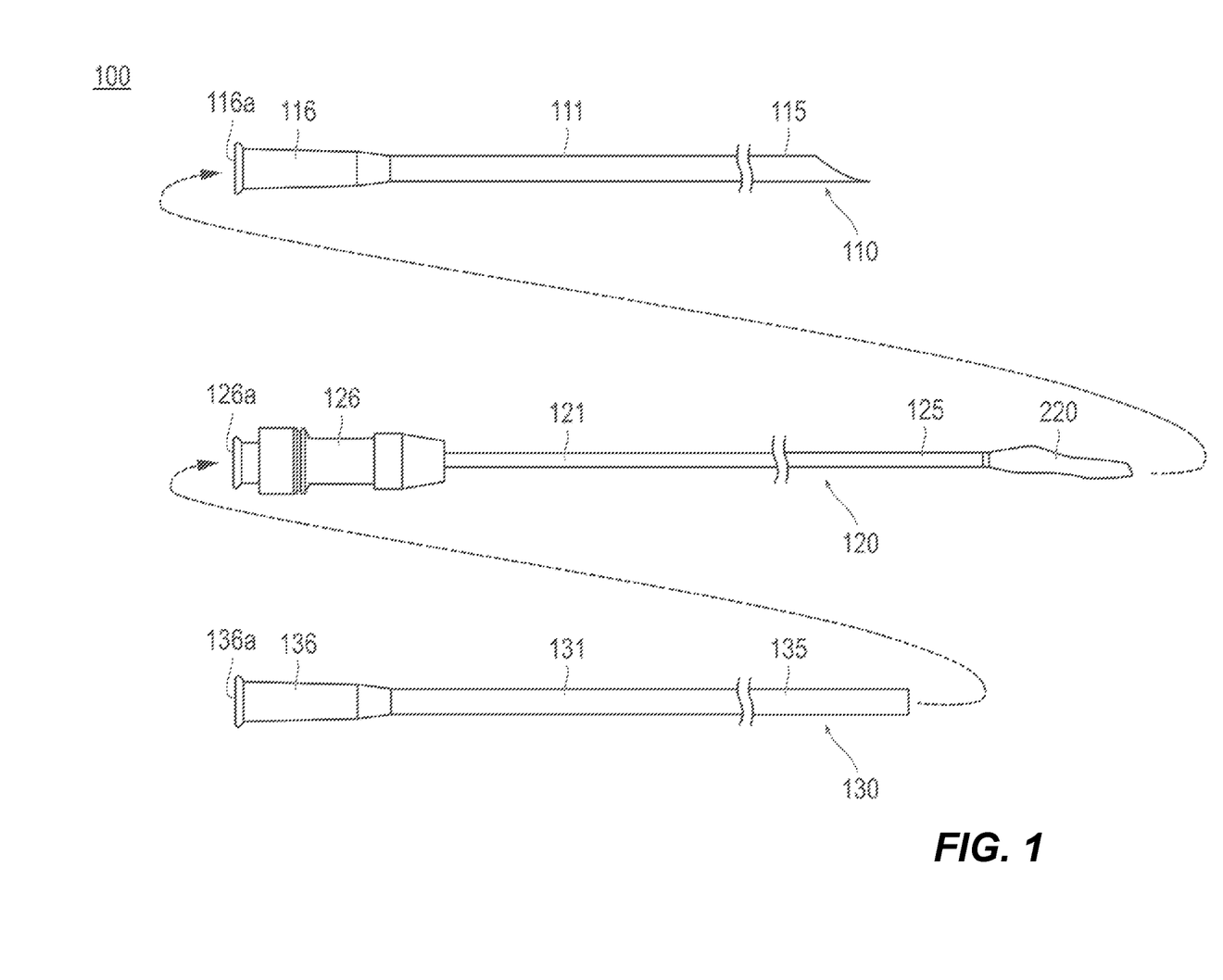
FIG. 1 is a diagram illustrating a medical device according to an embodiment.
Figure 2A:
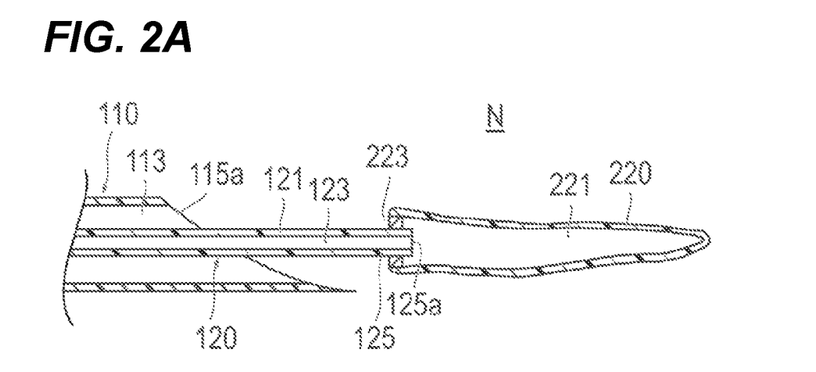
FIG. 2A is a cross-sectional view of an embodiment of a medical device in a first state.
Figure 2B:
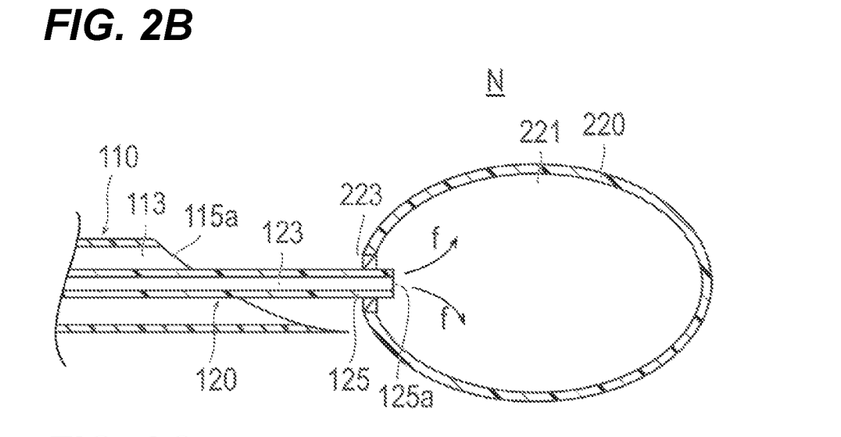
FIG. 2B is a cross-sectional view of an embodiment of a medical device in a second state.
Figure 2C:
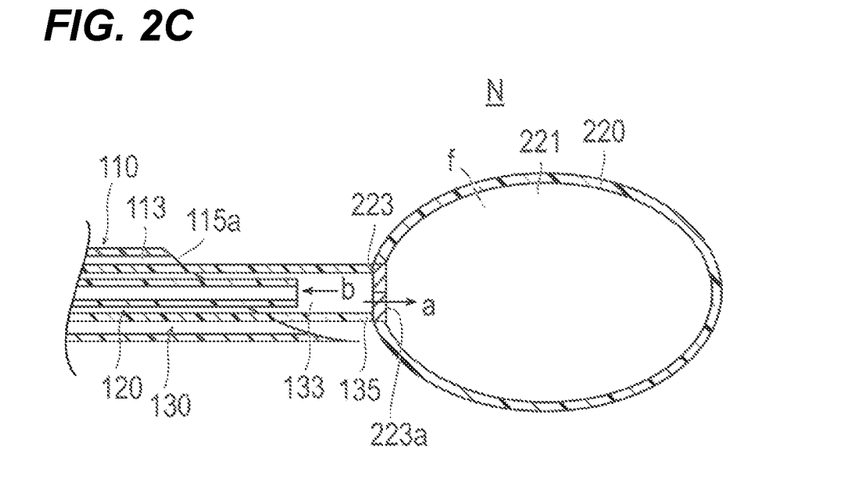
FIG. 2C is a cross-sectional view of an embodiment of a medical device in a third state.
Figure 3:
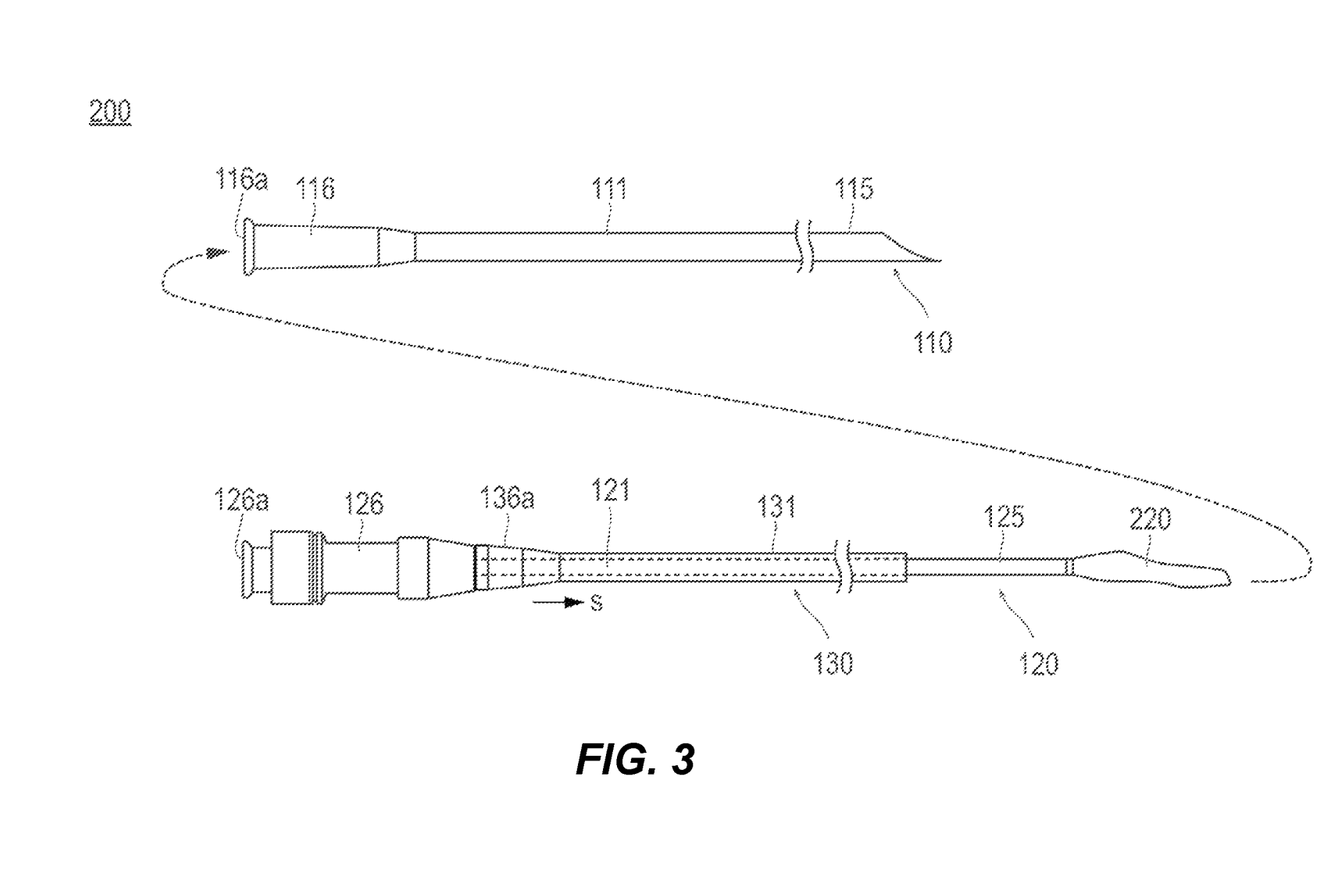
FIG. 3 is a diagram illustrating an embodiment of a medical device.
Figure 4:
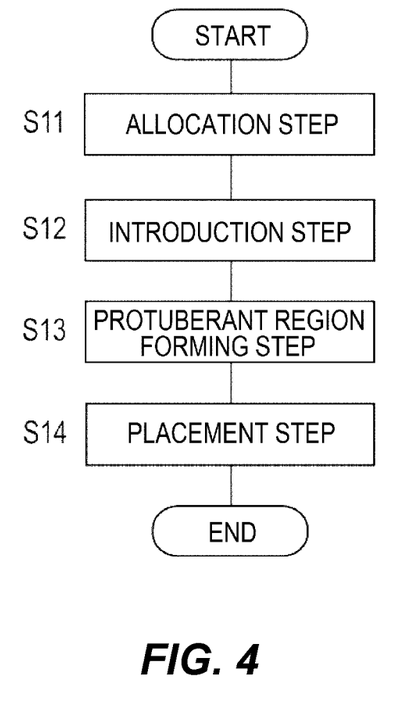
FIG. 4 is a flowchart illustrating an embodiment of a procedural method.

FIG. 1 and FIGS. 2A to 2C are diagrams illustrating, for example, configurations of various portions of a medical device 100 and a usage procedure for the medical device 100 according to an embodiment, FIG. 3 is a diagram illustrating a medical device 200 according to an embodiment, FIG. 4 is a flowchart illustrating steps of a procedural method according to the embodiment, and FIGS. 5A and 5B to FIGS. 7A and 7B are diagrams schematically illustrating the procedural method according to embodiments of the present disclosure.

As illustrated in FIGS. 5A and 5B and FIGS. 6A and 6B, an example is described in which the procedural method is applied to what is called breast augmentation, which forms a protuberant region (a distended region) in which the surface of a breast 320 protrudes from a body.

Furthermore, in the description of the present disclosure, the term "form a protuberant region" refers to forming a portion protruding on a biological superficial layer at the whole or apart of a biological organ (for example, the breast 320), which serves as a target for application, as viewed based on a comparison between before and after application of the procedural method.

An embodiment of the medical device 100 used in the procedural methods, is described.

As illustrated in FIG. 1, the medical device 100 is configured as a catheter assembly including three catheters, i.e., a first catheter 110, a second catheter 120, and a third catheter 130.

Moreover, in the description of the present disclosure, in the catheters 110, 120, and 130 included in the medical device 100, the side with which the introduction into the living body is performed is referred to as a "distal side", the hand-side at which each of hubs 116, 126, and 136 is mounted is referred to as a "proximal side", and the direction along which each of shafts 111, 121, and 131 extends is referred to as an "axial direction".

As described below, in the breast augmentation of the present embodiment, a container 220 attached to the distal portion 125 of the second catheter 120 is introduced into the breast 320, and then, a predetermined filling material f is introduced into the container 220 (refer to FIG. 2B and FIG. 6A). Then, the container 220 expansively deformed by being filled with the filling material, f, is placed in the breast 320 (refer to FIGS. 7A and 7B), so that the entire breast 320 is distended.

Figure 6A:
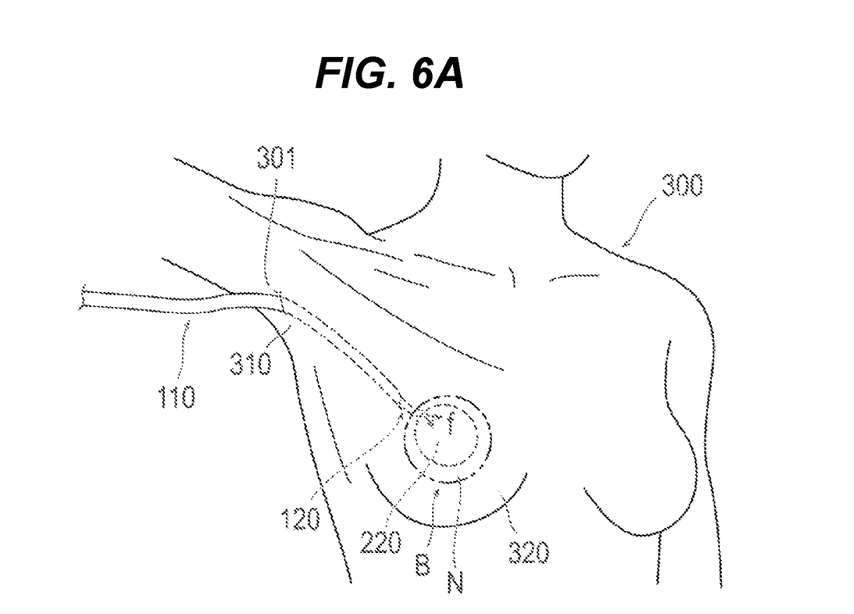
FIG. 6A is a third diagram illustrating an embodiment of the procedural method.

In the procedure performed in the above-described steps, the first catheter 110 may be used as a guiding catheter that forms a delivery route for delivering the container 220 included in the second catheter 120 to a predetermined placement site N (refer to FIG. 6(A)) in the breast 320. Furthermore, the second catheter 120 is used as a catheter that causes the container 220 attached to the distal portion 125 of the second catheter 120 to move along the inside of the first catheter 110. Moreover, as described below, the third catheter 130 is used as a catheter that is used when an operation for detaching the container 220 from the second catheter 120 is performed (refer to FIG. 2C).

The first catheter 110 is described.

As illustrated in FIG. 1, the first catheter 110 includes a shaft (first shaft) 111 extending in the axial direction and a hub 116 provided at the proximal portion of the shaft 111.

A needle tip (sharpened end portion) 115a is formed at the distal portion 115 of the shaft 111 of the first catheter 110 in such a way as to enable making a puncture in a living body. As illustrated in FIG. 2A, a lumen (first lumen) 113 extending in the axial direction is formed inside the shaft 111. A predetermined port 116a is provided at the proximal end of the hub 116.

The second catheter 120 is described.

The second catheter 120 includes a shaft (second shaft) 121 extending in the axial direction, a hub 126 provided at the proximal portion of the shaft 121, and a container 220 detachably attached to the distal portion 125 of the shaft 121.

As illustrated in FIG. 2A, a lumen (second lumen) 123 extending in the axial direction is formed inside the shaft 121. A predetermined port 126a is provided at the proximal end of the hub 126.

As illustrated in FIG. 2A, a distal end opening portion 125a of the shaft 121 of the second catheter 120 communicates with an internal space 221 of the container 220 in a liquid-tight manner. Therefore, as illustrated in FIG. 2B, when the filling material f is introduced into the lumen 123 of the shaft 121 of the second catheter 120, the filling material f flows into the internal space 221 of the container 220. The container 220 is expansively deformed in response to the inflow of the filling material f. The filling material f can be supplied from a supply device (omitted from illustration) connected to the port 126a via, for example, a predetermined tube (omitted from illustration). The supply device to be used includes, for example, a syringe pump or a known mechanically-driven pump.

The container 220 has a flexibility that allows expansive deformation to accommodate the inflow of the filling material f. The shapes of the container 220 taken before and after expansive deformation (the shape taken during delivery to the placement site N and the shape taken during placement at the placement site N) or the bulks thereof are not specifically limited, but can be set as appropriate according to, for example, a biological organ serving as a procedure target, a patient's request, or ease of performing a procedure.

In the present embodiment, the container 220 is made from a biodegradable material. The biodegradable material used to make the container 220 can be, for example, a known resin material having biodegradability, but is not limited to that. Furthermore, the period of degradation and disappearance of a biodegradable material can be set as appropriate according to, for example, the purpose of use of the container 220 (for example, a period of time for which to intend to maintain a state in which a protuberant region B desired by a patient is formed).

Moreover, the container 220 can be made from a material other than biodegradable materials. The material other than biodegradable materials to be used can be, for example, a material known as being used for a silicone bag or a balloon for balloon catheters.

The filling material f can be made from a material having such a fluidity as to allow inflow into the container 220. In the present embodiment, the material used to make the filling material f is gel-like hyaluronic acid, but is not limited to that and can be, for example, silicone. Additionally, the property of the filling material f can also be other than a gel-like property, and can be, for example, a granular property, a liquid property, or a property obtained by mixing liquid and gas.

The container 220 has a seal portion 223, which prevents the filling material f from leaking when the container 220 is detached from the second catheter 120 (refer to FIGS. 2B and 2C).

As illustrated in FIG. 2B, the seal portion 223 is provided in the vicinity of the distal end opening portion 125a of the second catheter 120. The seal portion 223 is configured to maintain a state in which the lumen 123 and the internal space 221 of the container 220 communicate with each other when the second catheter 120 has been inserted, and, on the other hand, when the second catheter 120 has been extracted, to form a hermetic sealing portion 223a along with such extraction (refer to FIG. 2C). The seal portion 223 can be made from, for example, an elastic member that is capable of performing self-sealing by elastically deforming along with extraction of the second catheter 120. However, the seal portion 223 can be composed of, for example, a mechanical valve which is capable of performing opening and closing operations in conjunction with insertion and extraction of the second catheter 120.

The third catheter 130 is described.

As illustrated in FIG. 1, the third catheter 130 includes a shaft (third shaft) 131 extending in the axial direction and a hub 136 provided at the proximal portion of the shaft 131.

As illustrated in FIG. 2C, a lumen (third lumen) 133 extending in the axial direction is formed inside the shaft 131. A predetermined port 136a is provided at the proximal end of the hub 136.

A usage procedure for the medical device 100 is described with reference to FIG. 1 and FIGS. 2A to 2C.

First, as illustrated in FIG. 2A, the first catheter 110 is inserted up to the vicinity of the placement site N in the living body. Next, the shaft 121 of the second catheter 120 to which the container 220 is attached is inserted into the lumen 113 of the first catheter 110. Then, the container 220 attached to the second catheter 120 is extruded from the needle tip 115a of the shaft 111 of the first catheter 110, and is thus placed at the placement site N.

Next, as illustrated in FIG. 2B, the filling material f is supplied via the lumen 123 of the second catheter 120 to expansively deform the container 220. Furthermore, the size of the container 220 taken after expansive deformation can be optionally changed and adjusted by adjusting the supplied amount of the filling material f.

As illustrated in FIG. 2C, after the container 220 is expansively deformed, the container 220 is placed at the placement site N. At this time, the distal portion 135 of the third catheter 130 is moved up to the vicinity of the seal portion 223 included in the container 220 via the lumen 113 of the first catheter 110. Then, an operation for pulling the second catheter 120 toward the proximal side as indicated by an arrow b illustrated in FIG. 2C while pushing the third catheter 130 toward the distal side as indicated by an arrow a illustrated in FIG. 2C is performed. This operation causes the shaft 121 of the second catheter 120 to be extracted from the seal portion 223 and causes the container 220 to be detached from the second catheter 120. After being detached from the second catheter 120, the container 220 is kept by the seal portion 223 in a liquid-tight state with the internal space 221 filled with the filling material f.

The insertion of the second catheter 120 into the first catheter 110 (refer to FIG. 2A) and the insertion of the third catheter 130 into a space between the first catheter 110 and the second catheter 120 (refer to FIG. 2C) can be performed via the port 116a provided at the first catheter 110 and the port 126a provided at the second catheter 120 as indicated by the arrows shown in FIG. 1. Each of the ports 116a and 126a can be provided with, for example, a valve body to prevent a body fluid in the living body (for example, blood) or the filling material f from flowing back and leaking.

While, for example, the inner diameter, outer diameter, and effective length (dimension in length along the axial direction) of each of the shafts included in the respective catheters 110, 120, and 130 are not specifically limited, for example, in a case where the medical device 100 is used for breast augmentation, the effective length of the shaft 111 of the first catheter 110 can be set to about 10 to 30 cm, and the effective lengths of the shaft 121 of the second catheter 120 and the shaft 131 of the third catheter 130 can be set longer than the effective length of the shaft 111 of the first catheter 110. The material used to form each of the shafts included in the respective catheters 110, 120, and 130 can be any material known as being used for shafts of various catheters.

Furthermore, for example, a medical device 200 illustrated in FIG. 3 can be used to perform a procedure for placing the container 220 and the filling material f. In the case of the medical device 200, the shaft 121 of the second catheter 120 is previously inserted into the shaft 131 of the third catheter 130. The hub of the third catheter 130 is provided with a connector 136a, which is connected to the hub 126 of the second catheter 120 with a known structure, such as a fitting type, a screw clamp type, and a push type (a type in which detachment is caused by a push operation). For example, after the filling material f is supplied, when the connection by the connector 136a is released, as illustrated in arrow s, the third catheter 130 can be moved forward along the shaft 121 of the second catheter 120. Moreover, an operation for moving the third catheter 130 forward can cause the shaft 121 of the second catheter 120 to be extracted from the seal portion 223 and cause the container 220 to be detached from the second catheter 120.

Next, an embodiment of a procedural method is described with reference to FIG. 4 and to FIGS. 7A and 7B.

As illustrated in FIG. 4, the procedural method, broadly described, includes an allocation step (S11), an introduction step (S12), a protuberant region forming step (S13), and a placement step (S14). Hereinafter, the respective steps are described in order.

Figure 5A:
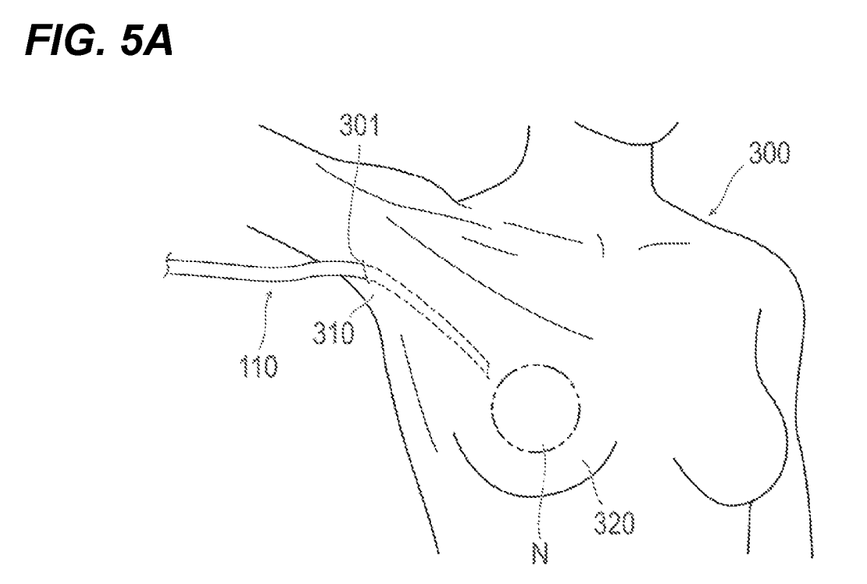
FIG. 5A is a first diagram illustrating an embodiment of the procedural method.

As illustrated in FIG. 5A, in the allocation step (S11), an operation for inserting the first catheter 110 into the living body 300 of a patient and allocating a delivery route leading to the placement site N at which to place the container 220 is performed. In one embodiment, the delivery route is the lumen 113 included in the shaft 111 of the first catheter 110 (refer to FIG. 2A).

As illustrated in FIG. 5A, in the allocation step (S11), the first catheter 110 is inserted, for example, in such a way as to lead from the axilla 310 of the living body 300 of the patient or the neighboring region of the axilla 310 to inside the breast 320 (breast region). Furthermore, prior to introduction of the first catheter 110, a predetermined perforation 301 is formed at an introduction position for the first catheter 110 using a medical instrument, such as a scalpel or an introducer.

Figure 5B:
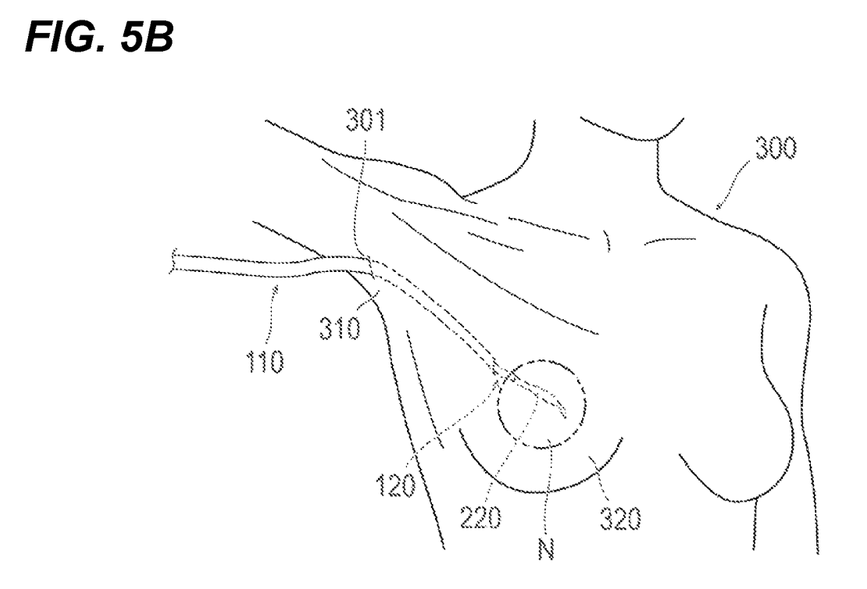
FIG. 5B is a second diagram illustrating an embodiment of the procedural method.

As illustrated in FIG. 5B, in the introduction step (S12), an operation for introducing the container 220 into the living body 300 of the patient is performed. At this time, as mentioned above, the container 220 is introduced up to the placement site N via the lumen 113 of the first catheter 110 (refer to FIG. 2A).

As illustrated in FIG. 6A, in the protuberant region forming step (S13), an operation for filling the container 220 with the filling material f to expand the container 220 and thus forming a protuberant region B, in which the surface of the living body (the surface of the breast 320) protrudes, is performed. At this time, as mentioned above, the filling material f is caused to flow into the container 220 via the lumen 123 of the second catheter 120 (refer to FIG. 2B).

Figure 6B:
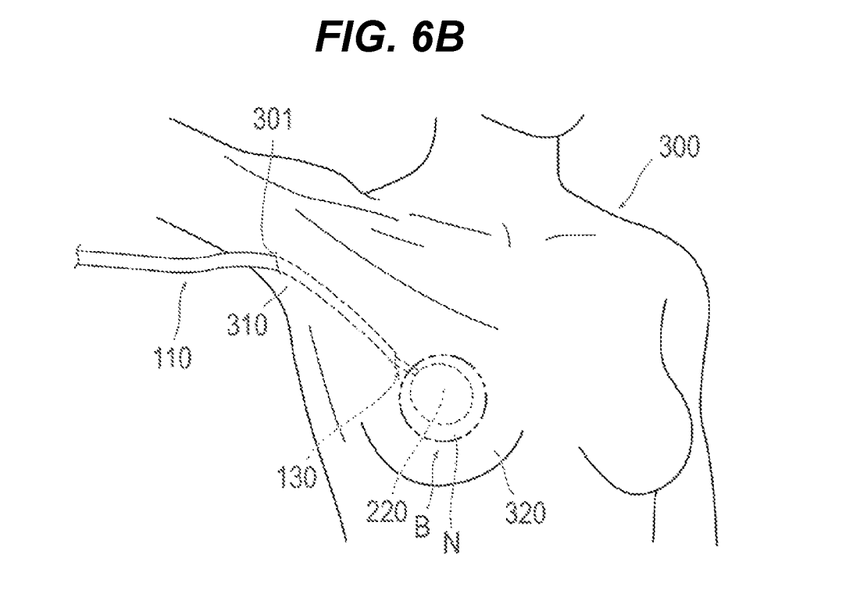
FIG. 6B is a fourth diagram illustrating an embodiment of the procedural method.

As illustrated in FIG. 6B, in the placement step (S14), an operation for placing the expanded container 220 in the living body is performed. In the present embodiment, after the protuberant region B is formed at the surface of the breast 320, the container 220 is placed in the breast 320. At this time, as mentioned above, the third catheter 130 is used to detach the container 220 from the second catheter 120 (refer to FIG. 2C).

After the container 220 is detached from the second catheter 120, the second catheter 120, the third catheter 130, and the first catheter 110 are extracted in this order. Furthermore, hemostasis is performed as appropriate by using, for example, suture on the perforation 301 formed as an introduction area for the first catheter 110. According to the above-described steps, breast augmentation can be completed.

Figure 7A:
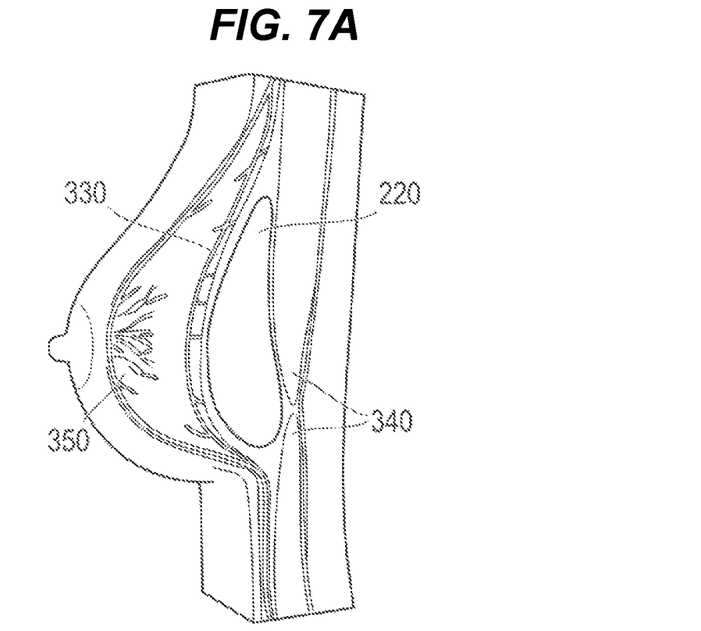
FIG. 7A is a cross-sectional view illustrating a state of a protuberant region after the procedural method is performed in accordance with embodiments of the present disclosure.
Figure 7B:
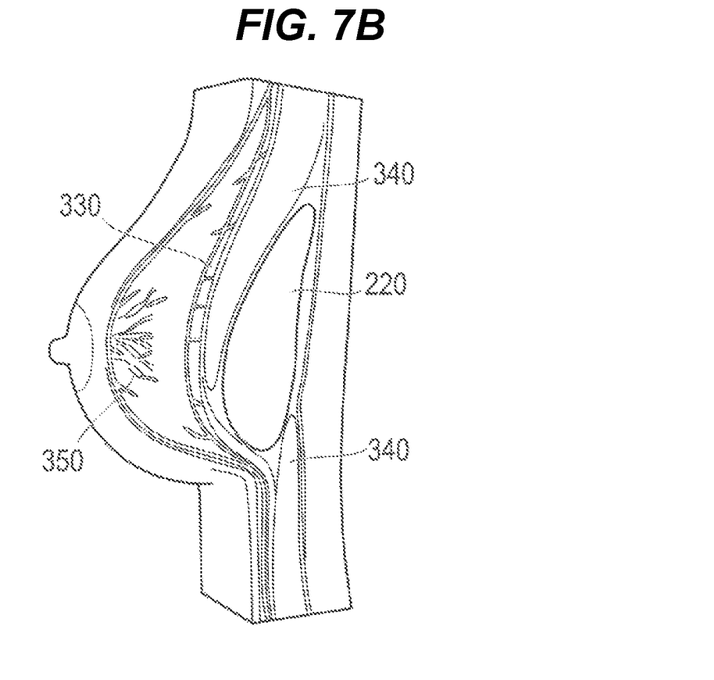
FIG. 7B is a cross-sectional view illustrating a state of a protuberant region after the procedural method is performed in accordance with embodiments of the present disclosure.

Furthermore, for example, the location at which to place the container 220 can be set to between the pectoralis major muscle 330 and the pleura 340 as illustrated in FIG. 7A, or can be set to between the adjacent pleurae 340 as illustrated in FIG. 7B. Moreover, although not illustrated, such a location can be set to between the mammary gland 350 and the pectoralis major muscle 330. Furthermore, after a procedure for one of the breasts 320 of the patient is completed, a procedure for another site (for example, the other breast 320) can be continuously performed, or an operation for placing another container 220 at a similar site can be continuously performed. Additionally, as the respective procedures are performed, containers 220 with different bulks can be placed or containers 220 with the same bulk can be placed.

As described above, the procedural method (breast augmentation) according to some embodiments of the present disclosure includes an introduction step (S12) of introducing a container 220 having flexibility into a living body 300, a protuberant region forming step (S13) of filling the container 220 with a filling material f to expand the container 220 and thus forming a protuberant region B, in which a surface of the living body 300 protrudes, and a placement step (S14) of placing the expanded container 220 in the living body 300.

In the above-described procedural method, the flexible container 220 in a contractive state is introduced into the living body 300, and, after being introduced, the container 220 is filled with the filling material f, so that the container 220 is expansively deformed. Then, the container 220 being expansively deformed in the living body 300 forms a protuberant region B, in which a surface of the living body 300 protrudes (distends). According to this procedure method, when the container 220 is introduced into the living body 300, since the inside of the container 220 is in an empty state, the bulk of the container 220 can be made small. This enables reducing the size of a perforation 301 which is formed on the living body 300 when the container 220 is introduced into the living body 300 and the size of a delivery route through which to deliver the container 220 to the placement site N (a delivery route which the first catheter 110 forms), so that a less-invasive procedure can be achieved. Furthermore, according to embodiments of the procedural method, since the filling material f is retained in the container 220, the filling material f can be prevented from undesirably dispersing or disappearing in the living body 300. Accordingly, the state of the expansively deformed container 220 can be stably maintained, and the state of the formed protuberant region B can be maintained in good condition over an intended period of time.

In conventional breast augmentation using fat of the patient himself or herself, in a case where the patient has no surplus fat and lacks usable fat, a procedure cannot be performed or a protuberant region formed by a single procedure may have a limitation in volume. In contrast to this, the procedural method according to the present embodiment enables relatively freely changing the volume of the placed protuberant region B by adjusting the supplied amount of the filling material f, so that the protuberant region B can be formed as desired by the patient.

In conventional breast augmentation using an indwelling object, such as a silicone bag, a feeling of strangeness may be caused after placement of the indwelling object, or pain may occur after surgery. Moreover, the edge of a silicone bag may graze in the living body or the behavior of a silicone bag may become unnatural. In contrast to this, the procedure method according to the present embodiment enables preventing pain from occurring after surgery since the indwelling object is composed of the flexible container 220 and the filling material f, and has a higher superiority in medical technology than the breast augmentation using a silicone bag or the like since a natural behavior is achieved using, for example, the flowage of the filling material f.

In a method of directly injecting hyaluronic acid or the like into the living body, since absorption and dispersion in the living body are uncontrollable, a duration of the formed protuberant region B may be short in some cases. In contrast to this, the procedural method according to the present disclosure enables preventing an unintended dispersion or disappearance of the filling material f from occurring since, as mentioned above, the container 220 having flexibility is filled with the filling material f, so that the state of the formed protuberant region B can be stably maintained.

Furthermore, embodiments of the procedural method may include, ahead of the introduction step (S12), an allocation step (S11) of inserting the first catheter 110 into the living body 300 and allocating a delivery route leading to the placement site N at which to place the container 220. Then, in the introduction step (S12), the second catheter 120, to which the container 220 is detachably attached, is inserted through the lumen 113 of the first catheter 110 to deliver the container 220 to the placement site N. Moreover, in the protuberant region forming step (S13), the container 220 is filled with the filling material f via the lumen 123 of the second catheter 120. Furthermore, in the placement step (S14), the container 220 is detached from the second catheter 120 and, then, the container 220 is placed in the living body 300.

Accordingly, since the procedure using the first catheter 110 and the second catheter 120 enables forming the protuberant region B, a less-invasive procedure using catheters can be achieved.

Furthermore, in some embodiments of the procedural method, in the allocation step (S11), the first catheter 110 may be inserted in such a way as to lead from the axilla 310 of the living body 300 or the neighboring region of the axilla 310 to inside the breast 320. Then, in the introduction step (S12), the container 220 can be delivered to inside the breast 320. Moreover, in the protuberant region forming step (S13), the protuberant region B may be formed at the surface of the breast 320. Furthermore, in the placement step (S14), the container 220 is placed in the breast 320.

Accordingly, breast augmentation can be achieved by a less-invasive procedure using catheters.

Moreover, in some embodiments of the procedural method, the container 220 may be made from a biodegradable material. Then, hyaluronic acid is used as the filling material f.

Accordingly, the state of the formed protuberant region B can be maintained according to a period for which the container 220 is decomposed and absorbed in the living body 300. Since the state of the formed protuberant region B is able to be controlled according to a request from, for example, a patient, a high-convenience procedure can be provided. Furthermore, since hyaluronic acid is used as the filling material f, the filling material f can be absorbed and vanished without an excess burden being imposed on the living body after decomposition and absorption of the container 220.

Furthermore, embodiments of the medical device 100 may include a first catheter 110 configured to be inserted into a living body 300 and a second catheter 120 having a distal portion 125 to which a container 220 having flexibility is detachably attached. Then, the first catheter 110 includes a first lumen 113 through which to deliver the container 220 of the second catheter 120 to a predetermined placement site N in the living body 300. Moreover, the second catheter 120 includes a second lumen 123 through which to deliver a filling material f to inside the container 220. Furthermore, the container 220 forms a protuberant region B, in which a surface of the living body protrudes, by being detached from the second catheter 120 and placed at the placement site N in a state of being filled with the filling material f.

According to the above-mentioned medical device 100, a procedure using the first catheter 110, the second catheter 120, and the container 220 having flexibility enables forming a protuberant region B, in which a surface of the living body 300 protrudes (distends). A perforation 301 and a delivery route are formed on and in the living body 300 in respective sizes corresponding to the dimension (the dimension of a cross-section perpendicular to the axis) of the first catheter 110. Moreover, the dimension of the first catheter 110 can be set small such that the size of the first catheter corresponds to the size or the bulk of the container 220 in an empty state. Accordingly, a burden imposed on the living body 300 in forming the protuberant region B can be reduced, so that a less-invasive procedure can be achieved. Furthermore, according to the medical device 100, since the filling material f is retained in the container 220, the filling material f can be prevented from undesirably dispersing or disappearing in the living body 300. Accordingly, the state of the expansively deformed container 220 can be stably maintained, and the state of the formed protuberant region B can be maintained in good condition over an intended period of time.

Furthermore, in the medical device 100, the container 220 may have a seal portion 223, which prevents the filling material f from leaking when the container 220 is detached from the second catheter 120. Accordingly, after the container 220 is placed, the filling material f can be appropriately prevented from leaking from the container 220.

Moreover, the medical device 100 may include a third catheter 130 configured to assist in detaching the container 220 from the second catheter 120. Then, the container 220 is detached from the second catheter 120 by a push operation relatively performed on the third catheter 130 against the second catheter 120. Therefore, a simple operation using the third catheter 130 enables readily detaching the container 220 from the second catheter 120.

Furthermore, in the medical device 100, since the container 220 is made from a biodegradable material, the state of the formed protuberant region B can be maintained according to a period for which the container 220 is decomposed and absorbed in the living body 300. Since the state of the formed protuberant region B is able to be controlled according to a request from, for example, a patient, a high-convenience procedure can be provided.

Figure 8:
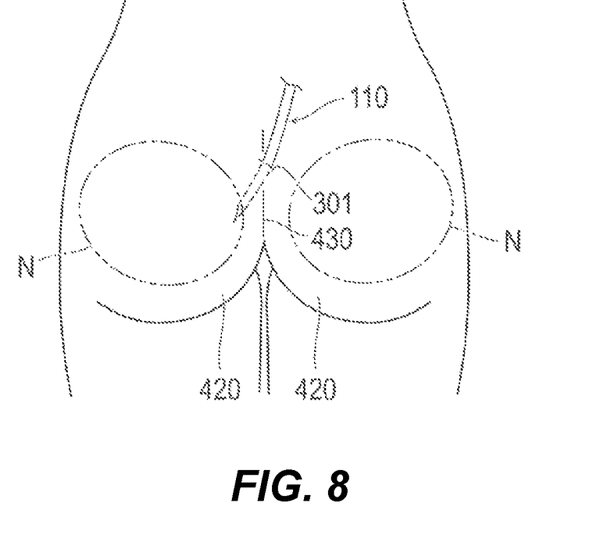
FIG. 8 is a diagram illustrating an embodiment of the procedural method.

As illustrated in FIG. 8, for example, an embodiment of the procedural method according to the present disclosure can be applied to buttock augmentation. In the buttock augmentation procedure, the following steps are performed.

Broadly described with reference to FIG. 4 and FIG. 8, in the allocation step (S11), the first catheter 110 is inserted in such away as to lead from the buttock 420 of the living body 300 or the neighboring region of the buttock 420 to inside the buttock 420. In the introduction step (S12), the container 220 is delivered to inside the buttock 420. In the protuberant region forming step (S13), a protuberant region B is formed at the surface of the buttock 420. In the placement step (S14), the container 220 is placed in the buttock 420.

A device similar to the above-described medical device 100 can be used in the procedural method described in conjunction with FIG. 8.

In the case of performing buttock augmentation, for example, a perforation 301 is formed in the vicinity of the intergluteal cleft 430, and, for example, the first catheter 110 is inserted through the perforation 301. The placement site N can be set to, for example, between the gluteus maximus muscle and the fascia inside the buttock 420.

Even when the procedural method of the present disclosure is applied to buttock augmentation, a less-invasive procedure can be achieved. Furthermore, since the filling material f is retained in the container 220, the state of the formed protuberant region B can be maintained in good condition over an intended period of time.

While embodiments of the procedural method and the medical device have been described above, the invention is not limited to only the methods and devices described above, but can be altered or modified as appropriate based on a recitation of claims.

For example, the procedural method according to the invention is applicable to sites other than the breast region and the buttock, which can be any site of the living body serving as a target in which a protuberant region is able to be formed. Furthermore, for example, the location through which the medical device is inserted into the living body is not limited to the locations described above (e.g., the axilla and the intergluteal cleft), and a delivery route leading to the placement site can also be changed as appropriate.

Moreover, the medical device for use in the procedural method only needs to include at least a configuration capable of placing a container filled with a filling material at an intended placement site, and such a configuration is not limited to the configurations described above with reference to the drawings. For example, imaging means (for example, an endoscope) can be used instead of the first catheter, and a container can be delivered to a placement site via, for example, a working channel of the imaging means.

Furthermore, for example, in a case where the patient is affected with subareolar abscess, a procedure for discharging pus causing the abscess can be performed.

For example, a procedure for approaching a pus area (affected area) in the breast region from the axilla and discharging pus to the outside of the body using a suction catheter or the like can be performed. In this procedure, for example, a suction catheter having a puncture needle can be used. In the case of using the suction catheter having a puncture needle, pus can be discharged by making a puncture in the pus area and performing suctioning with the puncture made in the pus area. Moreover, an operation for using a catheter having no puncture needle, causing the catheter to directly approach a pus area, and then discharging pus can be performed. Furthermore, an operation for supplying, for example, gas to the vicinity of a pus area using an endoscope and discharging pus in a state in which a space is kept. Additionally, not only an operation for discharging pus but also an operation for directly applying, for example, a medicine to a pus area can be performed.

DESCRIPTION OF REFERENCE NUMERALS AND SIGNS 100, 200 medical device,
110 first catheter,
111 shaft (first shaft),
113 lumen (first lumen),
120 second catheter,
121 shaft (second shaft),
123 lumen (second lumen),
130 third catheter,
131 shaft (third shaft),
133 lumen (third lumen),
220 container,
221 internal space,
223 seal portion,
300 living body of a patient,
310 axilla,
320 breast,
330 pectoralis major muscle,
340 pleura,
350 mammary gland,
420 buttock,
430 intergluteal cleft,
f filling material,
B protuberant region,
N placement site.

What is claimed is:

1. A procedural method comprising:
an allocation step of inserting a first catheter into a living body of a patient and allocating a delivery route leading to a placement site inside the living body, wherein the first catheter is maintained in a position adjacent to the placement site;
an introduction step of introducing a container having flexibility into the living body via the delivery route by moving the container from a position inside a lumen of the first catheter to a position outside of the lumen and at the placement site inside the living body while the first catheter is maintained in the position adjacent to the placement site, wherein a second catheter to which the container is detachably attached is inserted through the lumen of the first catheter to deliver the container to the placement site;
a protuberant region forming step of forming a protuberant region, in which a surface of the living body protrudes, by filling the container with a filling material to expand the container at the placement site inside the living body and, while the protuberant region is at the placement site, changing a volume of the protuberant region by adjusting a supplied amount of the filling material flowing through a lumen of the second catheter and into the container such that the protuberant region is formed as desired by the patient; and
a placement step of placing the expanded container in the living body by causing the expanded container to indwell at the placement site inside the living body, wherein the placement step comprises detaching the expanded container from the second catheter while the first catheter is maintained in the position adjacent to the placement site, and wherein a seal portion of the expanded container self-seals upon extracting the second catheter from the living body forming a hermetic seal for the expanded container.

2. The procedural method according to claim 1, wherein in the placement step, the expanded container is detached from the second catheter by pushing a third catheter, that is arranged at least partially inside the lumen of the first catheter, into contact with the expanded container and extracting the second catheter from the expanded container separating the expanded container from the second catheter inside the living body while the first catheter is maintained in the position adjacent to the placement site.

3. The procedural method according to claim 2, wherein, in the allocation step, the first catheter is inserted in such a way as to lead from an axilla of the living body or a vicinity of the axilla to inside a breast region,
in the introduction step, a perforation corresponding to a dimension of a cross-section perpendicular to an axis of the first catheter is made in the living body and the container is delivered to inside the breast region via the perforation in an empty state having no filling material disposed therein, in the protuberant region forming step, the protuberant region is formed at a surface of the breast region, and in the placement step, the container is placed in the breast region in a filled state.

4. The procedural method according to claim 2, wherein, in the allocation step, the first catheter is inserted in such a way as to lead from a buttock of the living body or a vicinity of the buttock to inside the buttock, in the introduction step, the container is delivered to inside the buttock, in the protuberant region forming step, the protuberant region is formed at a surface of the buttock, and in the placement step, the container is placed in the buttock.

5. The procedural method according to claim 1, wherein the container is made from a biodegradable material, and hyaluronic acid is used as the filling material.

* * * * *